(12) United States Patent
Stinson

(10) Patent No.: US 8,256,439 B1
(45) Date of Patent: Sep. 4, 2012

(54) DENTAL FLOSS DISPENSER WITH WATER RESERVOIR AND ASSOCIATED METHOD

(76) Inventor: Kevin L. Stinson, Long Beach, CA (US)

( * ) Notice: Subject to any disclaimer, the term of this patent is extended or adjusted under 35 U.S.C. 154(b) by 261 days.

(21) Appl. No.: 12/703,210

(22) Filed: Feb. 10, 2010

Related U.S. Application Data

(60) Provisional application No. 61/207,205, filed on Feb. 9, 2009.

(51) Int. Cl.
*A61C 15/00* (2006.01)
(52) U.S. Cl. ........................................ 132/324; 132/325
(58) Field of Classification Search ........... 132/324–326
See application file for complete search history.

(56) References Cited

U.S. PATENT DOCUMENTS

| 3,830,247 | A | * | 8/1974 | Kaphalakos | .................. 132/322 |
| 4,019,522 | A | | 4/1977 | Elbreder | |
| 5,076,302 | A | | 12/1991 | Chari | |
| 6,705,328 | B1 | * | 3/2004 | Ramirez | ....................... 132/322 |

* cited by examiner

*Primary Examiner* — Rachel Steitz

(57) ABSTRACT

A dental floss dispenser may include a portable container body having an interior cavity with a non-linear reservoir formed inside the interior cavity and situated along an interior perimeter of the container body. A spool may be rotatably coupled to the container body and seated inside the interior cavity. A predetermined volume of fluid may be housed inside the reservoir. A predetermined quantity of floss may further be releasably wound about the spool. A leading end of the floss may be channeled through the reservoir and thereby soaked in the fluid prior to exiting the container body. The apparatus may include a lid pivotally coupled to the container body. A floss guide and a floss cutter may be located inside the container body and situated above the reservoir exterior of the interior cavity for directing the floss away from the container body.

15 Claims, 4 Drawing Sheets

DENTAL FLOSS DISPENSER WITH WATER RESERVOIR AND ASSOCIATED METHOD

CROSS REFERENCE TO RELATED APPLICATIONS

This application claims the benefit of U.S. Provisional Application No. 61/207,205, filed Feb. 9, 2009, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to oral hygiene products and, more particularly, to a dental floss dispenser with water reservoir for providing users with an easy and convenient means of wetting the floss with fluid disinfectant to render it more comfortable and hygienic for use.

2. Prior Art

Proper hygiene is a key factor in maintaining a healthy and happy existence. Reducing germs and bacteria, hygiene practices are important for making a person feel clean and fresh on a daily basis. Taking a quick shower or enjoying a long, hot soak in the bathtub, are some activities that can cleanse the body and refresh the spirit. In particular, maintaining proper oral hygiene is crucial to ensure overall good health. Although most adults realize the considerable role daily brushing plays in maintaining health, many overlook the importance of using dental floss. Flossing between the teeth after each meal is an absolute must, if one wishes to keep their breath fresh, teeth clean, and gums healthy. Brushing teeth properly and consistently helps to remove most dental plaque; however, brushing alone cannot remove plaque that is located in places that a toothbrush cannot reach, particularly in between teeth. In addition to removing plaque, flossing also helps to dislodge debris that adheres to teeth and gums, and serves to polish the teeth. Most dentists recommend that flossing should take place at least once a day for two to three minutes each time to be most effective.

Unfortunately, flossing the teeth can be a difficult and unsettling task, simply because the rigid, dry floss can cause discomfort when sliding between the teeth and against the gums. As such, many consumers opt to skip this important hygiene procedure, only to be diagnosed with cavities or other forms of tooth decay on their next visit to the dentist office.

Accordingly, a need remains for an apparatus in order to overcome the above-noted shortcomings. The present invention satisfies such a need by providing a dental floss dispenser with fluid reservoir that is convenient and easy to use, is durable yet lightweight in design, is versatile in its applications, and provides an easy and convenient means of wetting the floss with fluid disinfectant to render it more comfortable and hygienic for use.

BRIEF SUMMARY OF THE INVENTION

In view of the foregoing background, it is therefore an object of the present invention to provide an apparatus for promoting dental hygiene. These and other objects, features, and advantages of the invention are provided by a dental floss dispenser.

The dental floss dispenser may include a portable container body preferably having an interior cavity. A non-linear reservoir may be formed inside the interior cavity and situated along an interior perimeter of the container body. A spool may be rotatably coupled to the container body and seated inside the interior cavity. A predetermined volume of fluid may be housed inside the reservoir. A predetermined quantity of floss may further be releasably wound about the spool. A leading end of the floss may be channeled through the reservoir and thereby soaked in the fluid prior to exiting the container body. The spool may remain isolated from the reservoir such that a remaining portion of the floss is maintained at a dry state. Such an arrangement provides the unexpected and unpredictable advantage of wetting and softening the dental floss as it is being pulled out from the dental floss dispenser. In this way, the dental floss 11 may be wetted with the fluid 24 and made soft so that it can be easily inserted between a user's teeth.

The dental floss dispenser may further include a lid pivotally coupled to the container body. A floss guide may be located inside the container body and situated above the reservoir. A floss cutter may further be connected to the floss guide. The floss guide and the floss cutter may further be situated exterior of the interior cavity for directing the floss away from the container body. Such an arrangement provides the unexpected and unpredictable advantage of guiding the dental floss away from the portable container body and thereafter, allowing a user to cut a desired length for use easily without having to utilize another cutting appliance.

The leading end of the floss may travel along a first passageway located interior of the reservoir before exiting the container body. The first passageway may include first, second and third linear segments conjoined at an end-to-end pattern and extending within the reservoir respectively. The leading end of the floss may further travel along a second passageway located exterior of the reservoir. The second passageway may include a fourth linear segment extending away from the third linear segment and the reservoir respectively. The fourth linear segment may be channeled through the floss guide along a travel path registered parallel to the second linear segment. In this way, the leading end of the floss may be maintained in a wet environment within the fluid while traveling along the first, second and third linear segments; and be maintained in a dry environment while traveling along the fourth linear segment. Such an arrangement provides the unexpected and unpredictable advantage of providing an unimpeded path for the dental floss and to be automatically wetted prior to exiting the dental floss dispenser.

The fluid may include at least two disinfecting agents selected from a group including mouthwash, water, fluoride and any combination thereof. Such an arrangement provides the unexpected and unpredictable advantage of providing a dual use for the dental floss including disengaging leftover food and debris stuck between a user's teeth and disinfecting a user's teeth and gums simultaneously.

The reservoir may include an access port for depositing and draining the fluid from the reservoir while the leading end of the floss remains housed inside the reservoir. An inlet port may be formed at a first top end of the cavity and disposed at a beginning of the first linear segment. An outlet port may be formed at a second top end of the cavity and disposed at an end of the third linear segment. In this way, the leading end of the floss may ingress the reservoir via the inlet port and thereafter may egress the reservoir via the outlet port prior to reaching the floss guide. Such an arrangement provides the unexpected and unpredictable advantage of holding the fluid in the reservoir as well as providing a channel for the dental floss to be wetted within a water tight assembly.

The reservoir may further include a first guide pulley rotatably situated at a junction of the first and second linear segments and a second guide pulley rotatably situated at a junction of the second and third linear segments respectively. In this way, each of the first and second guide pulleys may maintain continuous contact with the leading end of the floss and thereby continuously direct the leading end of the floss along the first, second and third linear segments inside the reservoir respectively. Such an arrangement provides the unexpected and unpredictable advantage of ensuring that the dental floss may be smoothly extracted from the container body without being entangled in any way.

The first and third linear segments may further have coextensive longitudinal lengths and are registered parallel to each other, while the second and fourth linear segments have coextensive longitudinal lengths and are registered parallel to each other. Such an arrangement provides the unexpected and unpredictable advantage of providing a box-shaped and compact enclosure whereby a user may rest the apparatus upright on a side of the container body corresponding to the second segment of the reservoir. In this way, the user may make doubly sure that the fluid contained within the reservoir may not egress from the inlet and outlet ports of the container cavity.

The invention may include a method of utilizing a dental floss dispenser for promoting dental hygiene. Such a method may include the chronological steps of: providing a portable container body preferably having an interior cavity formed therein; providing a non-linear reservoir formed inside the interior cavity and situated along an interior perimeter thereof; providing and seating a spool inside the interior cavity by rotatably coupling the spool to the container body; providing and housing a predetermined volume of fluid inside the reservoir; providing and releasably winding a predetermined quantity of floss about the spool; providing for soaking a leading end of the floss in the fluid prior to exiting the container body by channeling the leading end of the floss through the reservoir; and providing for maintaining a remaining portion of the floss at a dry state by isolating the spool from the reservoir. There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
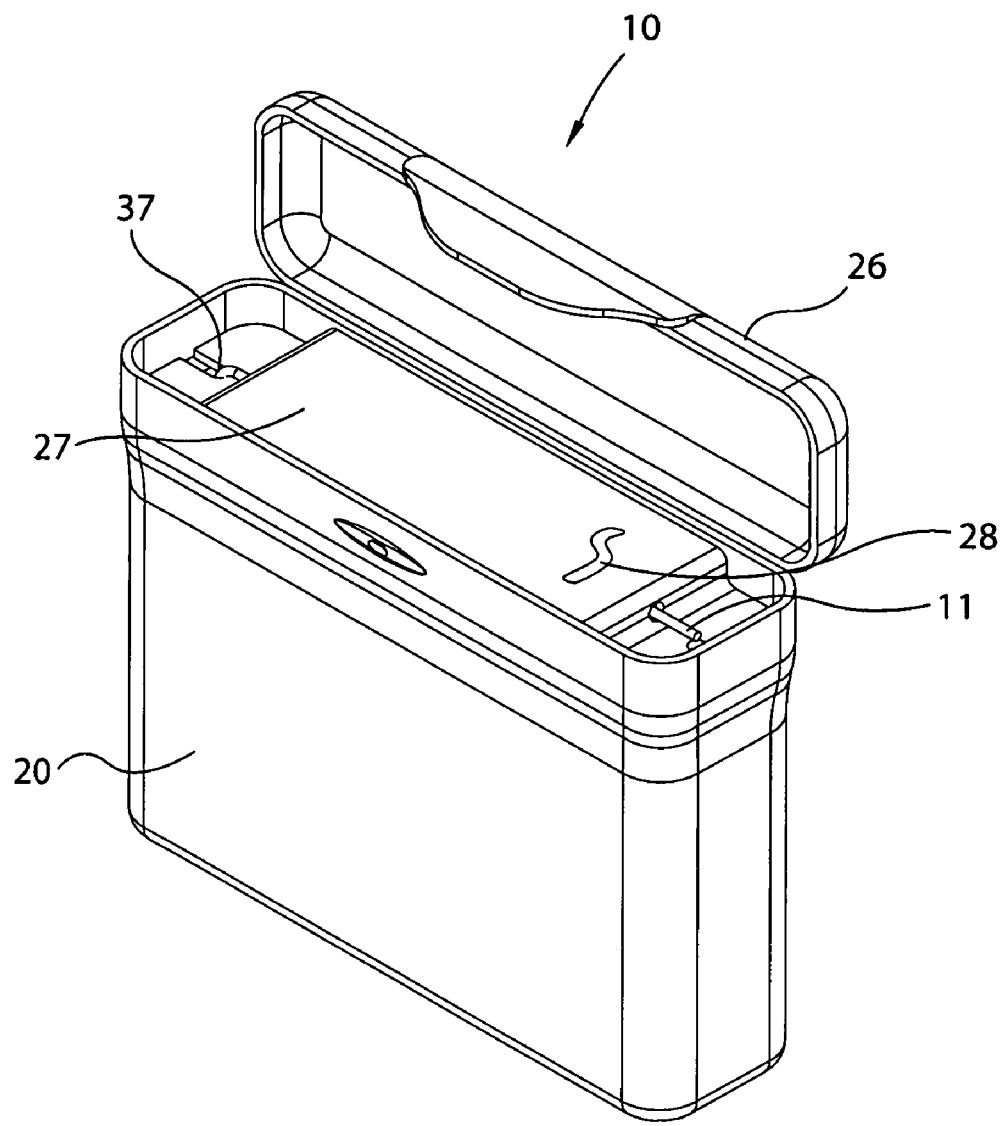
FIG. 1 is a perspective view showing a dental floss dispenser, in accordance with the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The apparatus of this invention is referred to generally in FIGS. 1-4 by the reference numeral 10 and is intended to provide a dental floss dispenser. It should be understood that the dental dispenser 10 may be used to provide a dental floss and many different types of stringed implements that is soft, wet and hygienic for use.

Referring generally to FIGS. 1-4, the dental floss dispenser 10 may include a portable container body 20 preferably having an interior cavity 21. A non-linear reservoir 22 may be formed inside the interior cavity 21 and situated along an interior perimeter of the container body 20. A spool 23 may be rotatably coupled to the container body 20 and seated inside the interior cavity 21. A predetermined volume of fluid 24 may be housed inside the reservoir 22. A predetermined quantity of floss 11 may further be releasably wound about the spool 23. In this manner, a leading end of the floss 11 may be channeled through the reservoir 22 and thereby soaked in the fluid 24 prior to exiting the container body 20. Advantageously, the spool 23 remains isolated from the reservoir 22 such that a remaining portion of the floss 11 is maintained at a dry state. Such an arrangement provides the unexpected and unpredictable advantage of wetting and softening the dental floss 11 as it is being pulled out from the apparatus 10. In this way, the dental floss 11 may be wetted with the fluid 24 and made soft so that it can be easily inserted between a user's teeth.

Referring again to FIGS. 1-4, the dental floss dispenser 10 may further include a lid 26 pivotally coupled to the container body 20. A floss guide 27 may be located inside the container body 20 and situated above the reservoir 22. A floss cutter 28 may be connected to the floss guide 27. The floss guide 27 and the floss cutter 28 may be situated exterior of the interior cavity 21 for directing the floss 11 away from the container body 20. Such an arrangement provides the unexpected and unpredictable advantage of guiding the dental floss 11 away from the portable container body 20 and thereafter, allowing a user to cut a desired length after the floss 11 is soaked.

Figure 4:
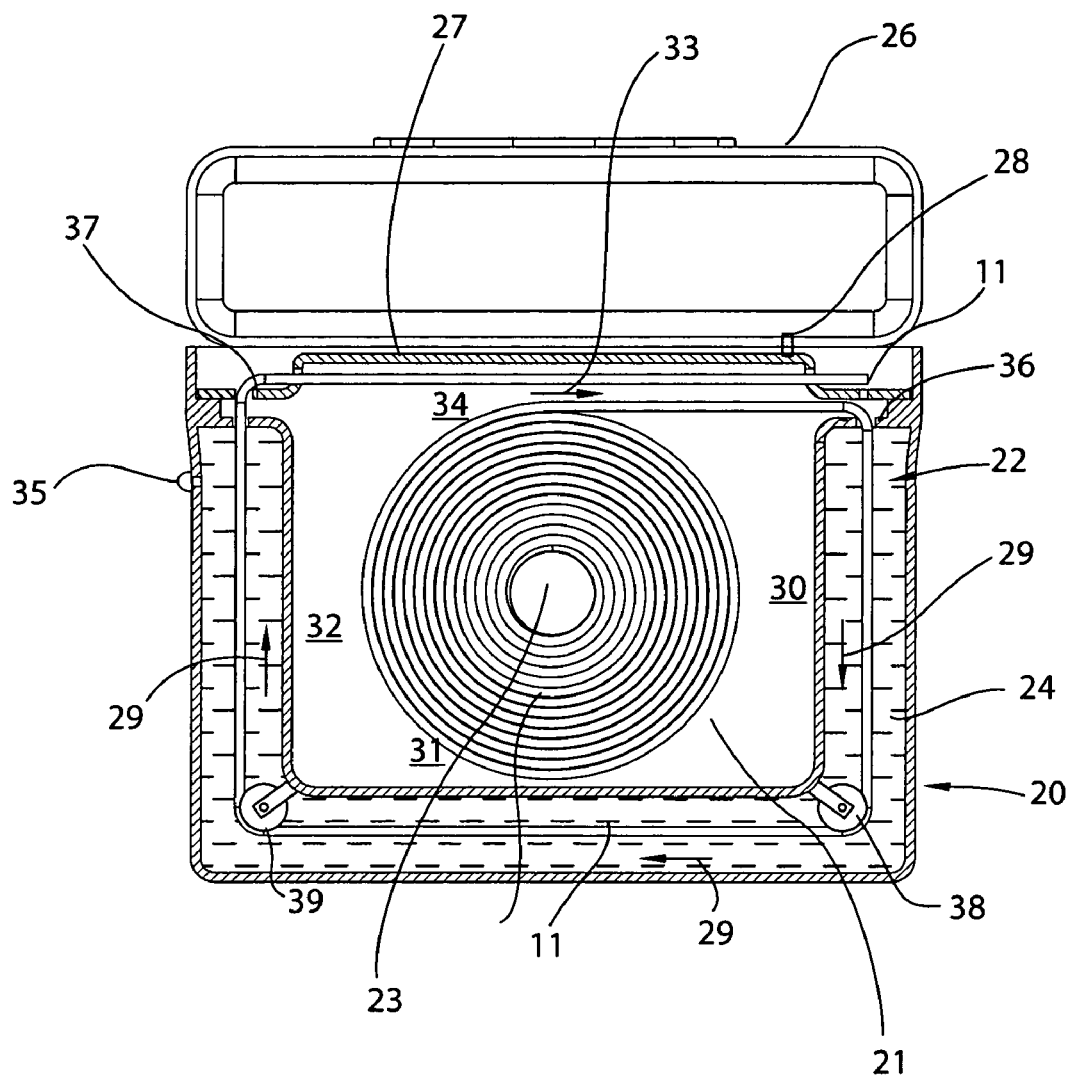
FIG. 4 is a cross-sectional view of the apparatus along line 4-4 shown in FIG. 3.

As perhaps best shown in FIG. 4, the leading end of the floss 11 may travel along a first passageway 29 located interior of the reservoir 22 before exiting the container body 20. The first passageway 29 may include a first linear segment 30, a second linear segment 31, and third linear segment 32 conjoined at an end-to-end pattern and extending within the reservoir 22, respectively. The leading end of the floss 11 may further travel along a second passageway 33 located exterior of the reservoir 22. The second passageway 33 may include a fourth linear segment 34 extending away from the third linear segment 32 and the reservoir 22, respectively. The fourth linear segment 34 may be channeled through the floss guide 27 along a travel path registered parallel to the second linear segment 31. In this way, the leading end of the floss 11 is advantageously maintained in a wet environment within fluid 24 while traveling along the first, second and third linear segments 30, 31, 32, respectively, and maintained in a dry environment while traveling along the fourth linear segment 34. Such an arrangement provides the unexpected and unpredictable advantage of providing an unimpeded wet passageway 29 for dental floss 11 wherein excess fluid 24 is wiped from floss 11 along the dry passageway 33 prior to exiting the apparatus 10 so that fluid residue is not deposited exterior of the container body 20

Referring to FIG. 4 again, the fluid 24 may include at least two disinfecting agents selected from a group including mouthwash, water, fluoride and any combination thereof. Such an arrangement provides the unexpected and unpredictable advantage of soaking floss 11 in a disinfectant fluid prior to expelling floss 11 from container body 20.

Figure 2:
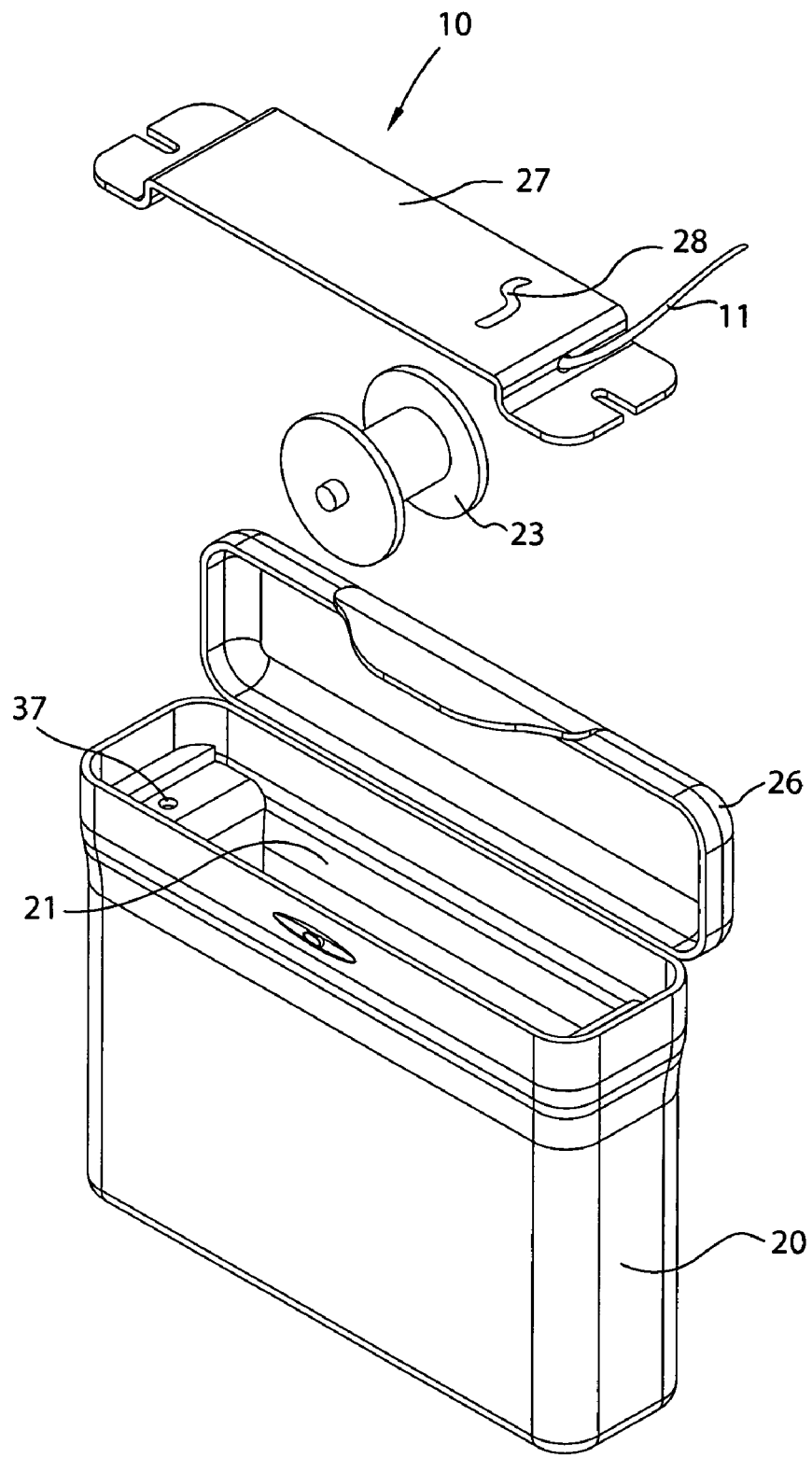
FIG. 2 is an exploded view of the apparatus shown in FIG. 1.
Figure 3:
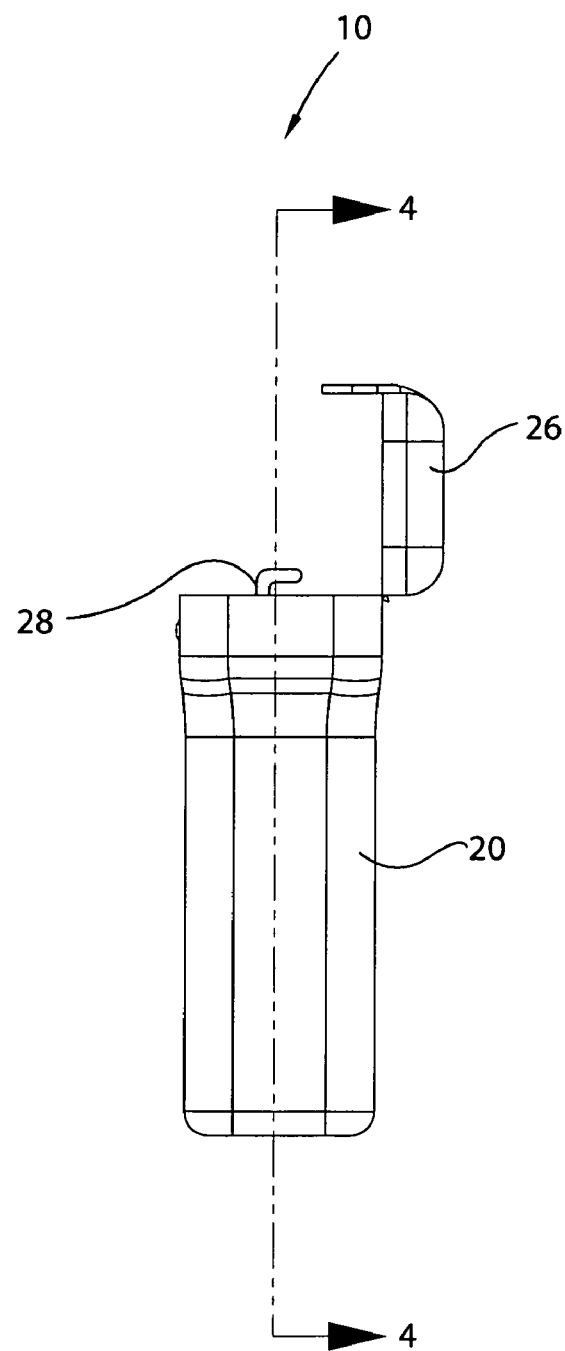
FIG. 3 is a side elevational view of the apparatus shown in FIG. 1.

Referring to FIGS. 2-4, the reservoir 22 may include an access port 35 for depositing and draining the fluid 24 from the reservoir 22 while the leading end of the floss 11 remains housed inside the reservoir 22. An inlet port 36 may be formed at a first top end of the cavity 21 and disposed at a beginning of the first linear segment 30. An outlet port 37 may be formed at a second top end of the cavity 21 and disposed at an end of the third linear segment 32. In this manner, the leading end of floss 11 ingresses reservoir 22 via inlet port 36 and thereafter egresses reservoir 22 via outlet port 37 prior to reaching floss guide 27. Such an arrangement provides the unexpected and unpredictable advantage of holding the fluid 24 in the reservoir 22 as well as providing a channel for the dental floss 11 to be wetted prior to being cut by floss cutter 28.

Referring to FIGS. 1, 2 and 4, the reservoir 22 may further include a first guide pulley 38 rotatably situated at a junction of the first and second linear segments 30, 31 and a second guide pulley 39 rotatably situated at a junction of the second and third linear segments 31, 32, respectively. In this way, each of the first and second guide pulleys 38, 39 maintain continuous contact with the leading end of floss 11 and thereby continuously direct the leading end of the floss 11 along the first, second and third linear segments 30, 31, 32 inside reservoir 22, respectively. Such an arrangement provides the unexpected and unpredictable advantage of ensuring that the dental floss 11 is smoothly extracted from the container body 20 without being entangled or rubbed against an interior wall of reservoir 22 during the unwinding process.

Referring again to FIG. 4, the first and third linear segments 30, 32 may further have coextensive longitudinal lengths and are registered parallel to each other, while the second and fourth linear segments 31, 34 have coextensive longitudinal lengths and are registered parallel to each other. Such an arrangement provides the unexpected and unpredictable advantage of providing a box-shaped and compact enclosure whereby a user may rest the apparatus 10 upright on a side of the container body 20 corresponding to the second segment 31 of the reservoir 22. In this way, the fluid 24 remains contained within the reservoir 22 and will not prematurely leak out form inlet and outlet ports 36, 37 of the container cavity 21.

The present invention may further include a method of utilizing a dental floss dispenser 10 for promoting dental hygiene. Such a method may include the chronological steps of: providing a portable container body 20 preferably having an interior cavity 21 formed therein; providing a non-linear reservoir 22 formed inside the interior cavity 21 and situated along an interior perimeter thereof; providing and seating a spool 23 inside the interior cavity 21 by rotatably coupling the spool 23 to the container body 20; providing and housing a predetermined volume of fluid 24 inside the reservoir 22.

The method may further include the chronological steps of: providing and releasably winding a predetermined quantity of floss 11 about the spool 23; soaking a leading end of the floss 11 in fluid 24 prior to exiting the container body 20 by channeling the leading end of the floss 11 through the reservoir 22; and maintaining a remaining portion of the floss 11 at a dry state by isolating the spool 23 from the reservoir 22.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The combination of such claimed elements provides an unpredictable and unexpected benefit of wetting a dental floss hygienically while removing it from the dental floss dispenser, which solves the problem of having to position the floss under a bottle of disinfectant or running tap to wet and soften the floss.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A dental floss dispenser for promoting dental hygiene, said dental floss dispenser comprising:
    a container body having an interior cavity formed therein;
    a reservoir formed inside said interior cavity and situated along an interior perimeter thereof;
    a spool rotatably coupled to said container body and seated inside said interior cavity;
    a predetermined volume of fluid housed inside said reservoir; and
    a predetermined quantity of floss releasably wound about said spool;
    wherein a leading end of said floss is channeled through said reservoir and thereby soaked in said fluid prior to exiting said container body;
    wherein said spool remains isolated from said reservoir such that a remaining portion of said floss is maintained at a dry state;
    a lid pivotally coupled to said container body;
    a floss guide located inside said container body and situated above said reservoir; and
    a floss cutter connected to said floss guide;
    wherein said floss guide and said floss cutter are situated exterior of said interior cavity for directing said floss away from said container body;
    wherein said leading end of said floss travels along a first passageway located interior of said reservoir before exiting said container body, said first passageway including first, second and third linear segments conjoined at an end-to-end pattern and extending within said reservoir respectively;
    wherein said leading end of said floss further travels along a second passageway located exterior of said reservoir, said second passageway including a fourth linear segment extending away from said third linear segment and said reservoir respectively, said fourth linear segment being channeled through said floss guide along a travel path registered parallel to said second linear segment;
    wherein said leading end of said floss is maintained in a wet environment within said fluid while traveling along said first, second and third linear segments, said leading end of said floss being maintained in a dry environment while traveling along said fourth linear segment.

2. The dental floss dispenser of claim 1, wherein said fluid comprises: at least two disinfecting agents selected from a group including mouthwash, water, fluoride and any combination thereof.

3. The dental floss dispenser of claim 2, wherein said reservoir comprises:
    an access port for depositing and draining said fluid from said reservoir while said leading end of said floss remains housed inside said reservoir;
    an inlet port formed at a first top end of said cavity and disposed at a beginning of said first linear segment;
    an outlet port formed at a second top end of said cavity and disposed at an end of said third linear segment;
    wherein said leading end of said floss ingresses said reservoir via said inlet port and thereafter egresses said reservoir via said outlet port prior to reaching said floss guide.

4. The dental floss dispenser of claim 3, wherein said reservoir further comprises:
    a first guide pulley rotatably situated at a junction of said first and second linear segments; and
    a second guide pulley rotatably situated at a junction of said second and third linear segments;
    wherein each of said first and second guide pulleys maintaining continuous contact with said leading end of said floss and thereby continuously direct said leading end of said floss along said first, second and third linear segments inside said reservoir respectively.

5. The dental floss dispenser of claim 4, wherein said first and third linear segments have coextensive longitudinal lengths and are registered parallel to each other, wherein said second and fourth linear segments have coextensive longitudinal lengths and are registered parallel to each other.

6. A dental floss dispenser for promoting dental hygiene, said dental floss dispenser comprising:
    a portable container body having an interior cavity formed therein;
    a non-linear reservoir formed inside said interior cavity and situated along an interior perimeter thereof;
    a spool rotatably coupled to said container body and seated inside said interior cavity;
    a predetermined volume of fluid housed inside said reservoir; and
    a predetermined quantity of floss releasably wound about said spool;
    wherein a leading end of said floss is channeled through said reservoir and thereby soaked in said fluid prior to exiting said container body;
    wherein said spool remains isolated from said reservoir such that a remaining portion of said floss is maintained at a dry state.

7. The dental floss dispenser of claim 6, further comprising:
    a lid pivotally coupled to said container body;
    a floss guide located inside said container body and situated above said reservoir; and
    a floss cutter connected to said floss guide;

wherein said floss guide and said floss cutter are situated exterior of said interior cavity for directing said floss away from said container body.

8. The dental floss dispenser of claim 7, wherein said leading end of said floss travels along a first passageway located interior of said reservoir before exiting said container body, said first passageway including first, second and third linear segments conjoined at an end-to-end pattern and extending within said reservoir respectively.

9. The dental floss dispenser of claim 8, wherein said leading end of said floss further travels along a second passageway located exterior of said reservoir, said second passageway including a fourth linear segment extending away from said third linear segment and said reservoir respectively, said fourth linear segment being channeled through said floss guide along a travel path registered parallel to said second linear segment.

10. The dental floss dispenser of claim 9, wherein said leading end of said floss is maintained in a wet environment within said fluid while traveling along said first, second and third linear segments, said leading end of said floss being maintained in a dry environment while traveling along said fourth linear segment.

11. The dental floss dispenser of claim 10, wherein said fluid comprises: at least two disinfecting agents selected from a group including mouthwash, water, fluoride and any combination thereof.

12. The dental floss dispenser of claim 11, wherein said reservoir comprises:
an access port for depositing and draining said fluid from said reservoir while said leading end of said floss remains housed inside said reservoir;
an inlet port formed at a first top end of said cavity and disposed at a beginning of said first linear segment;
an outlet port formed at a second top end of said cavity and disposed at an end of said third linear segment;
wherein said leading end of said floss ingresses said reservoir via said inlet port and thereafter egresses said reservoir via said outlet port prior to reaching said floss guide.

13. The dental floss dispenser of claim 12, wherein said reservoir further comprises:
a first guide pulley rotatably situated at a junction of said first and second linear segments; and
a second guide pulley rotatably situated at a junction of said second and third linear segments;
wherein each of said first and second guide pulleys maintaining continuous contact with said leading end of said floss and thereby continuously direct said leading end of said floss along said first, second and third linear segments inside said reservoir respectively.

14. The dental floss dispenser of claim 13, wherein said first and third linear segments have coextensive longitudinal lengths and are registered parallel to each other, wherein said second and fourth linear segments have coextensive longitudinal lengths and are registered parallel to each other.

15. A method of utilizing a dental floss dispenser for promoting dental hygiene, said method comprising the chronological steps of:
providing a portable container body having an interior cavity formed therein;
providing a non-linear reservoir formed inside said interior cavity and situated along an interior perimeter thereof;
providing and seating a spool inside said interior cavity by rotatably coupling said spool to said container body;
providing and housing a predetermined volume of fluid inside said reservoir;
providing and releasably winding a predetermined quantity of floss about said spool;
soaking a leading end of said floss in said fluid prior to exiting said container body by channeling said leading end of said floss through said reservoir; and
maintaining a remaining portion of said floss at a dry state by isolating said spool from said reservoir.

\* \* \* \* \*